| United States Patent [19] | [11] | 4,351,762 |
|---|---|---|
| Verlander et al. | [45] | Sep. 28, 1982 |

[54] RAPID, QUANTITATIVE PEPTIDE SYNTHESIS USING MIXED ANHYDRIDES

[75] Inventors: Michael S. Verlander, Del Mar; William D. Fuller, San Diego; Murray Goodman, La Jolla, all of Calif.

[73] Assignee: BioResearch, Inc., Farmingdale, N.Y.

[21] Appl. No.: 242,310

[22] Filed: Mar. 10, 1981

[51] Int. Cl.³ .......................................... C07C 103/52
[52] U.S. Cl. ............................................ 260/112.5 R
[58] Field of Search ................................ 260/112.5 R

[56] References Cited

U.S. PATENT DOCUMENTS 2,713,045 7/1955 Wieland et al. ............. 260/112.5 R
2,713,574 7/1955 Vaughan, Jr. ................ 260/112.5 R
2,715,119 8/1955 Wieland et al. ............. 260/112.5 R
4,267,344 5/1981 Halstrom et al. ............. 260/112.5 R

*Primary Examiner*—Delbert R. Phillips
*Attorney, Agent, or Firm*—Larson and Taylor

[57] ABSTRACT

In the synthesis of a polypeptide chain wherein an $N^\alpha$-urethane-protected amino acid mixed anhydride is coupled with an amino-unprotected second amino acid, the improvement comprising conducting said coupling at room temperature or above. This method provides rapid, essentially quantitative reactions without the necessity for reduced temperatures. The method is particularly useful in the solid-phase synthesis of peptides where shortened coupling cycles and improved yields of substantially pure products are obtained.

10 Claims, No Drawings

RAPID, QUANTITATIVE PEPTIDE SYNTHESIS USING MIXED ANHYDRIDES

FIELD OF THE INVENTION

This invention relates to the synthesis of peptides, polypeptides and proteins. More particularly, the invention is directed to an improvement in peptide, polypeptide and protein synthesis wherein the activated, N-protected amino acid employed in one or more coupling reactions of the synthesis is an $N^\alpha$-urethane-protected amino acid mixed anhydride.

BRIEF DESCRIPTION OF PRIOR ART

The classical method for the synthesis of peptides involves first coupling an $N^\alpha$-protected (and sidechain-protected if required) amino acid via its carboxyl group, to a similar or dissimilar amino acid containing an unprotected α-amino group. The protected or partially-protected dipeptide so formed is then isolated, purified and characterized completely before extending the peptide chain, in a stepwise manner, through appropriate deprotection and coupling reactions, with isolation and purification of intermediates at each step. Although in principle the peptide may be assembled either from the amino or carboxyl terminus, in practice the latter is preferred, mainly because of lower extents of racemization when $N^\alpha$-urethane-protected (and sidechain-protected where necessary), carboxyl-activated amino acids are used in coupling reactions.

In the solid-phase method for peptide synthesis, originally proposed by Merrifield [J. Amer. Chem. Soc. 85, 2149 (1963)] and Letsinger and Kornet [J. Amer. Chem. Soc. 85, 2045 (1963)] the peptide chain is assembled in a stepwise manner on an insoluble support. Through use of such a support, purification of intermediates at each step is effected through simple washing procedures and therefore isolation, purification and characterization of the intermediates (as is commonly required in the classical approach) is avoided.

Of the many known methods of carboxyl activation which are commonly used in peptide coupling reactions, the so-called "repetitive mixed anhydride method", developed by Tilak, has enjoyed considerable success. In this method, an $N^\alpha$-urethane-protected (sidechain-protected where necessary) amino acid (I) is activated by treatment with an acyl chloride or an alkyl, aralkyl or aryl chloroformate (II), in the presence of a tertiary base such as triethylamine or N-methylmorpholine to produce the mixed anhydride (III):

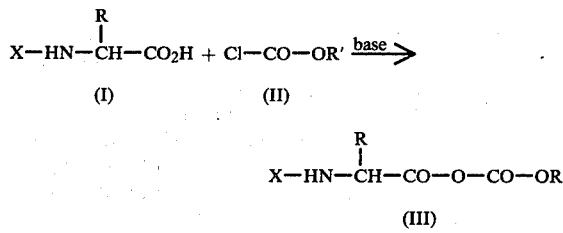

The formation of the mixed anhydrides (commonly referred to as "the activation step") is usually conducted at low temperatures (−10° to −30° C.). Coupling of these activated intermediates with, for example, a carboxyl-protected amino acid (IV) to give a protected dipeptide (V) is also carried out at reduced temperatures

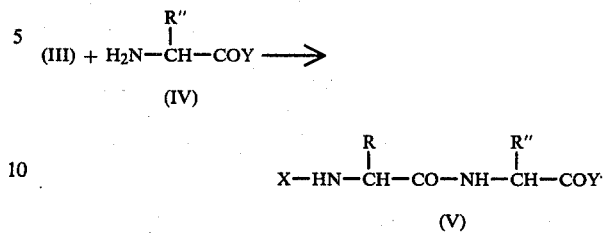

(less than 10° C. and preferably below 0° C.) because of the purported instability of the mixed anhydrides. This purported instability was demonstrated for the mixed anhydrides derived from acyl amino acids or peptides which tended to form cyclic intermediates (such as oxazolinones) which can undergo racemization or other decomposition reactions [see for example Vaughan and Osata, J. Amer. Chem. Soc. 74, 676 (1952); Albertson, Org. Reactions 12, 193 (1962); and Anderson et al., J. Amer. Chem. Soc. 86, 1839 (1964)]. Consequently, all syntheses using mixed anhydrides, including those derived from $N^\alpha$-urethane-protected amino acids, reported in the literature, have avoided use of elevated temperatures (i.e. room temperature and above), for fear of these side reactions.

Because of this purported instability of the mixed anhydrides and the inconvenience of conducting solid-phase syntheses at low temperatures, their use in solid-phase peptide synthesis has been severely restricted, despite the advantage of their high reactivity.

SUMMARY OF THE INVENTION

It has now been discovered that, contrary to the experiences of prior art syntheses of polypeptides, when the mixed anhydrides used in the synthesis are derived from $N^\alpha$-urethane-protected amino acids, reactions can be carried out at room temperature and above with unexpected advantages. These unexpected advantages include rapid, quantitative coupling reactions without detectable racemization. As a result of the rapid, quantitative couplings, decomposition and side reactions that normally occur during the prolonged coupling of conventional, activated amino acids are avoided.

Further studies have shown that mixed anhydrides derived from $N^\alpha$-urethane-protected amino acids, containing stable, unreactive sidechain protecting groups if required, formed pursuant to the current invention, and coupled one hour after activation at room temperature, give quantitative yields of peptides with no detectable racemization (see Example 2 and Table 1). In fact, mixed anhydrides are even stable to refluxing tetrahydrofuran (66° C., 1 hour) without detectable decomposition (see Example 5). Long-term stability studies have shown that the mixed anhydrides of $N^\alpha$-urethane-protected amino acids are stable at room temperatures for at least 24 hours and at 0° C. for at least 7 days (see Example 6 and Table 2).

Furthermore, it has been found that under certain conditions the mixed anhydrides of a number of amino acids are relatively slow to form or may not form at all, depending on the solvent and base used, unless the temperature is raised during activation. In dichloromethane as solvent and using triethylamine as base, the mixed anhydride of phenylalanine, for example, does not form completely, even after prolonged periods of −15° C., and the temperature must be raised to at least 0° C. before activation is complete. It is believed that in such cases what was thought by earlier workers in the field to be decomposition (i.e. stability), disproportionation or "wrong-opening" of the mixed anhydrides to give urethane-terminated sequences, may actually have been incomplete formation. If this were the case, the activating agent, (e.g. chloroformate) still present in the reaction mixture would acylate rapidly any amino acid, for example, during a subsequent coupling reaction, leading to the "wrong-opening" urethane derivative which would effectively lower the yield of the desired product.

In another aspect of the invention, a particularly advantageous use of mixed anhydrides at elevated temperatures is in the area of so-called solid-phase peptide synthesis. This method, discussed above, utilizes an insoluble support for the sequential assembly of the desired peptide from its carboxyl terminus, using $N^\alpha$-urethane-protected activated amino acid derivatives. However, this method often gives unsatisfactory yields of products which are difficult to purify because of the presence of closely-related contaminants (so-called "deletion peptides" or "failure sequences"). Apart from the inherent inhomogeneity of reactive sites on the insoluble matrix (commonly derivatized, crosslinked polystyrene) which can lead to incomplete reaction during coupling and deprotection steps, many side reactions can occur because of the long coupling times which are invariably used. For example, in the standard procedure, using dicyclohexylcarbodiimide activation, coupling times of 2-5 hours or more are commonly used. Even when activation via the symmetrical anhydride (a more reactive species than that derived from dicylohexylcarbodiimide) is used, coupling times of 1-2 hours are not unusual.

Amino acid mixed anhydrides are amongst the most activated of amino acid derivatives known and they have been used successfully in syntheses in solution since their introduction in the early 1950's. However, the use of mixed anhydrides in solid-phase syntheses has been limited to a small number of studies which have not been extended. Despite the recognition of the high reactivity of mixed anhydrides their use in solid-phase syntheses under the prior art conditions (i.e. at low temperatures) has provided less than desirable results because of unacceptably low coupling yields [see, for example, Tilak and Hollinden, Tetrahedron Lett., 1297 (1969) and Merrifield et al., J. Org. Chem. 39, 660 (1974)].

It has been surprisingly discovered that the poor performance of the mixed anhydrides in the prior art solid-phase peptide syntheses is due to the use of low temperature reaction conditions. In contrast, when mixed anhydrides are used at ambient temperature or above, unexpectedly high coupling yields are obtained in solid-phase and other polymer-supported syntheses. Reactions are extremely rapid and surprisingly are not accompanied by decomposition or racemization, invariably resulting in quantitative yields of homogeneous peptide products. The findings of the present invention enable the time required for the addition of a single amino acid residue to be substantially reduced (<30 minutes) compared with that required in conventional, solid-phase syntheses (up to 6 hours or more).

This aspect of the invention therefore involves an improvement in the synthesis of a polypeptide chain on a support containing reactive substituent groups, wherein an $N^\alpha$-urethane-protected amino acid coupled to the support by condensation with said reactive substituent groups is deprotected to provide a free $\alpha$-amino group on said coupled amino acid, a second, similar or dissimilar $N^\alpha$-urethane-protected amino acid in the form of its mixed anhydride is coupled to said $\alpha$-amino group and the deprotection and coupling processes repeated until the desired polypeptide is obtained, said improvement comprising conducting the mixed anhydride coupling reactions at room temperature and above.

In this aspect of the invention the preferred support is an insoluble support, in which case the synthesis is preferably carried out in a continuous flow reactor. Advantageously, the flow reactor is pressurized and the reactions in the flow reactor are conducted under a pressure of at least atmospheric pressure plus 25 psi (i.e. at least 40 psi), preferably in the range 100 to 1,000 psi, although pressures of up to 10,000 psi or more may be used.

DETAILED DESCRIPTION OF THE INVENTION

It should be understood that the term "polypeptides" as used in the specification and in the appended claims is meant to include peptides and proteins.

Any of the mixed anhydrides of $N^\alpha$-urethane-protected amino acids conventionally used in peptide synthesis can be employed in the present invention. Typical urethane-protected amino acids from which the mixed anhydrides are formed are $N^\alpha$-t-butyloxycarbonyl amino acids, $N^\alpha$-benzyloxycarbonyl amino acids, $N^\alpha$-biphenylisopropyloxycarbonyl amino acids and $N^\alpha$-9-fluorenylmethyloxycarbonyl amino acids. Illustrative of the amino acids thus urethane-protected are glycine, alanine, valine, leucine, isoleucine, phenylalanine, tryosine, serine, arginine, lysine, ornithine, glutamic acid, aspartic acid, histidine, tryptophan, proline and the like. It should be understood that an amino acid containing reactive sidechain functional groups should be protected at those functional groups so as to provide a stable, unreactive derivative.

The mixed anhydrides are derived by treating the $N^\alpha$-urethane-protected amino acid with a suitable activating agent capable of converting the urethane-protected amino acid to a urethane-protected amino acid mixed anhydride. Such activating agents include, for example, alkyl, aralkyl or aryl haloformates or acyl halides having the structure;

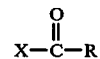

wherein X is halogen, preferably chlorine, and R is lower alkoxy, aralkoxy or aryloxy or lower alkyl, aralkyl or aryl. If a haloformate is used for activation, the resulting mixed anhydride is commonly referred to as "a mixed carboxylic-carbonic anhydride", whereas if an acyl halide is used for activation, the mixed anhydride is referred to as "a mixed carboxylic anhydride". Preferred haloformates are ethyl chloroformate and isobutyl chloroformate. The use of isobutyl chloroformate is most advantageous since the mixed anhydrides derived from this compound react extremely rapidly with the formation of completely innocuous by-products (carbon dioxide and isobutyl alcohol). A preferred acyl halide is pivaloyl chloride [$R=C(CH_3)_3$].

As aforementioned, the activation of the N$^\alpha$-urethane-protected amino acid is conveniently carried out in the presence of a tertiary base at room temperature (25° C.) but higher temperatures up to temperatures which render the resulting mixed anhydride unstable can be used, if desired.

In the peptide syntheses the mixed anhydrides are coupled to a similar or dissimilar amino acid whose carboxylic acid terminal group and sidechain functional groups are properly protected. Any of the suitable carboxyl-protecting groups, including carboxylate salts, which are well-known to those skilled in the peptide art can be used for this purpose. Again, any secondary reactive groups such as sidechain functional groups should be appropriately protected in this and subsequent couplings. One convenient method of protecting the carboxylic acid group is by esterification. While in the majority of cases the coupling reaction according to the invention proceeds rapidly at room temperature, higher temperatures up to the decomposition temperature of the mixed anhydride can be employed, if desired.

The remaining synthesis to form the desired polypeptide sequence is then carried out employing a series of deprotection, and coupling steps as described above. These operations will be discussed in more detail below in reference to the solid-phase aspect of the invention.

In syntheses of the invention wherein a support is utilized to build the polypeptide chain, the support can be either an insoluble support or a normally solid but solubilizable support. The insoluble solid supports can be any of those normally employed in the conventional, solid-phase syntheses, such as those utilized in the Merrifield technique, while the normally solid, solubilizable supports can be any of those employed in the so-called "liquid-phase method" for peptide synthesis, proposed by Bayer [see for example, Bayer and Mutter, Angew. Chem. 88, 101 (1974)].

In the solid-phase method of peptide synthesis according to the present invention, an insoluble solid support or matrix, advantageously in bead form, such as any of the conventional solid-phase polymeric substrates conventionally employed for the synthesis of polypeptides can be utilized. Typical of such polymeric resins are crosslinked polystyrene resins, crosslinked polyacrylamides, glass beads, clays, celite, crosslinked dextran, and similar insoluble solid supports which either naturally contain reactive sites for coupling with the amino acid components or which can be provided with such reactive sites. Insoluble supports particularly preferred are chloromethylated, crosslinked polystyrene resins, hydroxymethylated, crosslinked polystyrene resins, benzhydrylamine resins and the like. The crosslinked polystyrenes are normally copolymers of styrene and a crosslinking agent preferably formed by way of a pearl or bead polymerization process using an aqueous suspension system. Preferred crosslinking agents for preparation of the crosslinked polystyrene resins include divinyl compounds such as para-divinylbenzene, meta-divinylbenzene, divinylcyclohexane, butadiene, and the like.

In the liquid-phase method the polypeptide chain is assembled on a solubilized, linear polymeric support by conventional coupling and deprotection methods as used in both classical and solid-phase methods, described above. In order to effect purification of the growing peptide chain and removal of excess reagents and by-products in such liquid-phase methods, the solubilized polymeric support, with the attached, growing peptide chain, is precipitated, for instance by addition of a non-solvent, and washed as in the solid-phase method, and then resolubilized and the process repeated. Illustrative of suitable polymeric supports for such liquid-phase synthesis are linear polyethylene glycols, polyethylene glycol monoethers, linear polystyrenes and the like.

Several preliminary operations are necessary before the synthesis of a peptide can be started. First, the supporting resin containing the C-terminal amino acid of the proposed peptide chain must be prepared. The support containing the C-terminal amino acid may be prepared for instance by esterifying the amino acid with the reactive site or substituent group on the support such as chloromethylated or hydroxymethylated crosslinked polystyrene resins. The esterification reaction is accomplished directly with the chloromethylated resin by procedures well-established in the prior art or via suitable activation of the amino acid, such as with dicyclohexylcarbodiimide/dimethylaminopyridine or via the mixed anhydride with dimethylaminopyridine as catalyst as taught in this invention in the case of the hydroxymethylated resin. After the first C-terminal amino acid is coupled to the support, the resulting product is commonly analyzed using standard procedures such as quantitative amino acid analysis or nitrogen analysis to determine the amino acid content for the purpose of calculating the amounts of subsequent amino acid reactants and deprotecting agents to be used in the synthesis.

The remaining synthesis to form the desired polypeptide sequence is carried out as follows. Before coupling of the second amino acid residue can take place, the first residue already on the support must be deprotected. Deprotection of the first amino acid residue on the support as well as on each of the subsequently coupled amino acid residues can be carried out by treating the support with an appropriate deprotecting agent. The deprotecting agents employed for this purpose are well known to those of ordinary skill in the peptide synthesis art and the particular deprotecting agent employed in any given instance will depend of course upon the protecting group on the amino acid-support. For example, if the protecting group is t-butyloxycarbonyl, trifluoroacetic acid, methanesulfonic acid or hydrochloric acid in a suitable solvent such as dioxane or dichloromethane may be used. On the other hand, if the protecting group is biphenylisopropyloxycarbonyl, mild acidic conditions (e.g. 1% trifluoroacetic acid in a suitable solvent such as dichloromethane) are required. If the protecting group is 9-fluorenylmethyloxycarbonyl a secondary amine, such as piperidine or diethylamine in a suitable solvent such as dimethylformamide, is used for deprotection. The concentrations of the particular deprotecting agent in the solvent will vary depending again upon the particular protecting agent employed but will ordinarily range from about 5 to 50% by volume. A sufficient volume of deprotecting agent is employed for a period sufficient to ensure complete removal of the protecting group (generally 5–60 minutes is required).

After the deprotecting step, the support is washed with a suitable solvent, normally the solvent in which the deprotecting agent was dissolved, in order to remove excess deprotecting agent. If the deprotecting agent is an acid the peptide on the support must be neutralized by washing with an appropriate base such as triethylamine and the triethylammonium chloride or trifluoroacetate formed may be removed by repeated washings with a suitable solvent such as dichloromethane or dimethylformamide. The free α-amino group of the amino acid on the support, thus prepared, is now ready for coupling with the next protected amino acid.

A solution of the next N$^α$-urethane-protected amino acid activated as its mixed anhydride is then reacted with the support now containing an unprotected α-amino group on the C-terminal amino acid. In general, an excess of the activated, protected amino acid per equivalent of the first amino acid on the support is employed.

After coupling of the second protected amino acid to the first amino acid, the attached protected amino acid is then deprotected, neutralized (if necessary) and washed as described above before coupling of the next amino acid derivative is effected. This procedure is repeated until the desired sequence of amino acids has been assembled on the support.

In a particularly preferred aspect of the present invention solid-phase peptide syntheses are conducted in a flow reactor. Illustrative of such a suitable continuous flow reactor is the system described in Example 2 of U.S. Pat. No. 4,192,798, herein incorporated by reference. Use of such a reactor maximizes the efficiency of all of the operations in the synthetic cycle through application of the mass action effect, which forces reactions to completion, thereby maximizing both rates and yields in coupling and deprotection reactions. The flow reactor also facilitates washing operations and minimizes side reactions through efficient removal of excess reagents and by-products of reactions. Scale-up of syntheses is also more facile than in conventional, shaken reactors.

The entire series of coupling reactions in the above described methods, from the second amino acid (and if desired the first amino acid), to the last is conducted under a reactor pressure of 40 psi or more, preferably in the range of 100 to 1,000 psi. Reactor pressures of this level can be generated by use of commercial pressurizing equipment and methods. For example, any of the commercially available reciprocating pumps capable of generating the required pressures can be used and the reactants, reagents and wash solvents pumped directly into and through the reactor.

Alternatively, the reactants, reagents and wash solvents may be pumped through the reactor by means of pressurization with an inert gas such as nitrogen and the pressure in the reactor regulated by controlling the volume of inert gas released to transfer the reactants, reagents and wash materials into and through the reactor.

The completed peptide sequence can be removed from the support by any of the standard methods as, for instance, by cleavage with anhydrous hydrogen fluoride, transesterification, acidolysis, aminolysis, etc.

After cleavage, the resulting peptide is found to be remarkably homogeneous and to require no or minimal purification. Because of the very low contamination of by-products overall yields are found to be surprisingly high and whatever purification is necessary can be carried out with relative ease. Such purifications are preferably carried out by partition chromatography, ion exchange chromatography or a combination of both.

Illustrations of peptides, polypeptides and proteins which can be obtained by the method of the invention are enkephalins, angiotensin, oxytocin, vasopressin, luteinizing hormone releasing hormone, somatostatin, gastrin, insulin, glucagon, ribonuclease, endorphins, etc.

The following examples are included to further illustrate the present invention.

EXAMPLE 1

Stabilities of Mixed Anhydrides Under Standard Conditions—Synthesis of t-Butyloxycarbonyl-O-Benzyl Threonyl Leucine Methyl Ester The amino acid derivative, Boc-O-benzyl-L-threonine (3.09 g, 10 mmole) was dissolved in dry tetrahydrofuran (100 ml), and cooled to −15° C. with stirring. The infrared spectrum was recorded and isobutyl chloroformate (1.30 ml, 10 mmole) then added to the mixture. After maintaining the reaction mixture at −15° C. for 4 minutes the infrared spectrum was again recorded, when a strong absorption of 1810 cm$^{-1}$, characteristic of the mixed anhydride, was observed. After the 4 minute activation period leucine methyl ester hydrochloride (2.0 g, 11 mmole) was added to the mixture as a solid, followed by N-methylmorpholine (1.21 ml, 11 mmole). The infrared absorption at 1810 cm$^{-1}$ disappeared completely on addition of the leucine methyl ester. The reaction mixture was worked up after one hour by evaporating the solvent under reduced pressure and redissolving the residue in ethyl acetate:water (1:1, v/v). The phases were separated and the ethyl acetate layer further extracted 3 times with 10% citric acid, 3 times with saturated sodium bicarbonate, and finally twice with saturated sodium chloride. The organic layer was dried over magnesium sulfate before evaporation of the solvent to give a 98.6% isolated yield of crystalline product after thorough drying under vacuum. The product was shown to be completely homogeneous by reverse phase high performance liquid chromatography and contained none of the urethane side product corresponding to "wrong opening" of the mixed anhydride.

The stabilities of a variety of amino acid mixed anhydrides, as estimated by the yields the homogeneities of dipeptides formed under the "standard" conditions, are summarized in Table 1.

TABLE 1

| Stabilities of a Variety of Amino Acid Mixed Anhydrides as Measured by Synthesis of the Dipeptides, Boc—X—Leu—OBu$^t$ | | | |
|---|---|---|---|
| Amino Acid | Conditions$^a$ | Yield (%)$^b$ | Purity$^c$ |
| Boc—Phe | A | 96.7 | >99.5 |
| Boc—Phe | B | 98.5 | >99 |
| Boc—Val | A | 97.7 | — |
| Boc—Val | B | 95.9 | — |
| Boc—Pro | A | 95.3 | >99.5 |
| Boc—Pro | B | 95.6 | >99.5 |
| Boc—Thr(OBzl) | A | 98.6 | >99 |
| Boc—Thr(OBzl) | B | 97.2 | >99 |
| Boc—Met | A | 91.8 | >99.5 |
| Boc—Met | B | 99.2 | >99.5 |
| Boc—Lys(ε-Cbz) | A | 102 | — |
| Boc—Lys(ε-Cbz) | B | 101 | — |
| Boc—Asp(β-Bzl) | A | 103 | >99.5 |
| Boc—Asp(β-Bzl) | B | 103 | >99 |
| Fmoc—Phe | A | 101 | >99.5 |
| Fmoc—Phe | B | 102 | >99.5 |
| Fmoc—Val | A | 99.8 | >99.5 |
| Fmoc—Val | B | 101 | >99.5 |
| Bpoc—Ala | A | 98.9 | >99.5 |
| Bpoc—Ala | B | 99.2 | >99.5 |

$^a$Mixed anhydrides prepared using equimolar amounts of isobutylchloroformate and N-methylmorpholine in tetrahydrofuran as solvent at −15° C.; A = 5 minutes' activation at −15°, coupling at −15° (see Example 1); B = warm to 20° after activation, maintain at 20° for 1 hour then couple at 20° (see Example 2);
$^b$estimated from weight of crude product;
$^c$estimated from HPLC data.

EXAMPLE 2

Stabilities of Mixed Anhydrides at Room Temperature—Synthesis of t-Butyloxycarbonyl-O-benzyl Threonyl Leucine Methyl Ester The mixed anhydride of Boc-O-benzyl-L-threonine was generated at −15° C. as described above under Example 1. After addition of the isobutyl chloroformate the reaction mixture was maintained at −15° C. for 4 minutes. The temperature of the mixture was then allowed to rise to room temperature (25° C.) over approximately 30 minutes. The reaction mixture was stirred at room temperature for a further 60 minutes, during which no change in absorbance in the infrared spectrum between 2000 and 1500 cm$^{-1}$ was observed. At this point, leucine methyl ester hydrochloride (2.0 g, 11 mmole) was added as a solid to the reaction mixture at room temperature, followed by N-methylmorpholine (1.21 ml, 11 mmole). The absorbance at 1810 cm$^{-1}$ in the infrared spectrum (mixed anhydride) disappeared immediately. The reaction mixture was worked up in an identical manner to that described under Example 1, above, to give 97.2% of the dipeptide product which was shown to be completely homogeneous by reverse phase high performance liquid chromatography.

The stabilities of a variety of amino acid mixed anhydrides, determined in this manner, at room temperature, are summarized in Table 1 and compared with data for the same amino acid mixed anhydrides under "standard" conditions.

EXAMPLE 3

Racemization in Mixed Anhydride Coupling Reactions—Synthesis of t-Butyloxycarbonyl-L-phenylalanyl Leucine t-Butyl Ester The amino acid derivative, Boc-L-phenylalanine (1.33 g, 5 mmole) was dissolved in dry tetrahydrofuran (50 ml) and the mixed anhydride generated at −15° C., as described in earlier examples, by the addition of N-methylmorpholine (0.55 ml, 5 mmole) followed by isobutyl chloroformate (0.65 ml, 5 mmole). The reaction mixture was maintained at −15° C. for 4 minutes after addition of the chloroformate and then the cooling bath was removed and the mixture allowed to warm to room temperature. After one hour at this temperature leucine t-butyl ester hydrochloride (1.17 g, 6 mmole) was added as a solid, followed by N-methylmorpholine (0.66 ml, 6 mmole). A second reaction was performed on the same scale but under "standard" conditions, and the two worked up as described above under Example 1. After isolation, the crude products were dissolved in trifluoroacetic acid and stirred at room temperature for two hours, after which the trifluoroacetic acid was removed in vacuo, the residual oils redissolved in water and the samples lyophilized. Extents of racemization were estimated by reverse phase high performance liquid chromatography and were found to be undetectable in both cases.

EXAMPLE 4

Formation of Mixed Anhydrides at Room Temperature—Synthesis of t-Butyloxycarbonyl-L-phenylalanyl Leucine t-Butyl Ester The mixed anhydride of Boc-L-phenylalanine was formed as described under Example 3 by adding the base and chloroformate to the solution of the amino acid derivative at room temperature. After maintaining the reaction mixture at this temperature for one hour, the mixed anhydride was treated with leucine t-butyl ester as described under Example 3 and the product isolated and analyzed for yield and extent of racemization by the same procedure. The yield of product was quantitative (99%) and no racemization could be detected.

EXAMPLE 5

Stability of Mixed Anhydrides at Elevated Temperatures—Synthesis of Benzyloxycarbonyl-L-phenylalanyl Leucine t-Butyl Ester The mixed anhydride of benzyloxycarbonyl-L-phenylalanine was generated at room temperature as described in the above examples in tetrahydrofuran as solvent and using N-methylmorpholine as base. The reaction mixture was then refluxed (66° C.) for one hour before recooling to room temperature and treating with leucine t-butyl ester to form the dipeptide. Work-up and analysis of the product by the procedures already described gave an essentially quantitative yield of the product with no detectable racemization.

EXAMPLE 6

Long-term Stability of Mixed Anhydrides—Synthesis of t-Butyloxycarbonyl-L-phenylalanyl Leucine t-Butyl Ester The long-term stability of Boc-L-phenylalanine mixed anhydride was monitored by setting up a number of small-scale syntheses of the title compound using the procedure described under Example 4. Experiments were conducted with storage of the mixed anhydrides at both −2° C. and 25° C. and samples worked up by the procedures already described. The yields and extents of racemization of the product after various time periods were estimated as described above. The results of these studies, summarized in Table 2, indicate that this mixed anhydride is stable at room temperature for at least 24 hours and at −2° C. for at least 7 days.

TABLE 2

| Long-Term Stability of Boc—Phenylalanine Mixed Anhydrides[a] | | | |
|---|---|---|---|
| Period of Activation | Temperature | % D,L[b] | Purity (TLC) |
| 1 day | −2° C. | <1 | pure |
| 3 days | −2° C. | <1 | pure |
| 7 days | −2° C. | <1 | pure |
| 1 day | 25° C. | <1 | pure |
| 3 days | 25° C. | <1 | impure |
| 7 days | 25° C. | ~10 | impure |

[a]Estimated by formation of the dipeptide, Boc—L-phenylalanyl leucine t-butyl ester; see Example 4.
[b]Estimated by reverse phase high performance liquid chromatography.

EXAMPLE 7

Synthesis of L-Leucyl-L-Alanyl-Glycyl-L-Valine by the Solid-Phase Method Using Mixed Anhydrides at Room Temperature Fluorenylmethyloxycarbonyl-L-valine benzyloxybenzyl ester resin was prepared by the method of Wang [J. Amer. Chem. Soc. 95, 1328 (1973)]. The degree of substitution as estimated by the spectrophotometric assay of Meienhofer et al. [Int. J. Pept. Prot. Res. 13, 35 (1975)] was 0.55 mmoles of valine per gram of dry resin. This resin (0.6 g) was swollen in dry dimethylformamide (DMF) and the fluorenylmethyloxycarbonyl (Fmoc) group cleaved by treatment with 10% (v/v) piperidine in DMF (12 ml) for 10 minutes in a shaken vessel. The resin was then washed (6×10 ml DMF) and treated with a 0.1 M solution of Fmoc-glycine mixed anhydride (7 ml; 2.1 equivalents) in DMF for 10 minutes at room temperature. After washing the resin (DMF) the cleavage and coupling cycles were repeated using Fmoc-alanine and then Fmoc-leucine mixed anhydrides. The resin was finally treated with piperidine/DMF to cleave the terminal Fmoc-group before cleavage of the tetrapeptide from the resin by suspending in trifluoroacetic acid:dichloromethane (75:25, v/v; 15 ml) for 40 minutes at room temperature. Filtration and evaporation of the solvent resulted in a syrup which solidified on trituration with ether to give a quantitative yield (0.155 g) of the tetrapeptide, L-leucyl-L-alanyl-glycyl-L-valine. The product was shown to be homogeneous (i.e. >99% pure) by reverse phase high performance liquid chromatography, with no detectable contamination by "failure sequences" or urethane-terminated "wrong-opening" products (i.e. isobutyloxycarbonyl peptides).

It is claimed:

1. In the synthesis of a polypeptide chain on an insoluble solid support containing reactive substituent groups, wherein an $N^\alpha$-urethane-protected amino acid coupled to the support by condensation with said reactive substituent groups is deprotected to provide a free α-amino group on said coupled amino acid, a second, similar or dissimilar $N^\alpha$-urethane-protected amino acid in the form of its mixed anhydride is coupled to said α-amino group and the deprotection and coupling processes repeated until the desired polypeptide is obtained, the improvement wherein the mixed anhydride coupling reactions are conducted at room temperature and above.

2. A synthesis according to claim 1 wherein the mixed anhydride is an $N^\alpha$-t-butyloxycarbonyl amino acid mixed anhydride.

3. A synthesis according to claim 1 wherein the mixed anhydride is an $N^\alpha$-benzyloxycarbonyl amino acid mixed anhydride.

4. A synthesis according to claim 1 wherein the mixed anhydride is an $N^\alpha$-9-fluorenylmethyloxycarbonyl amino acid mixed anhydride.

5. A synthesis according to claim 1 wherein the mixed anhydride is an $N^\alpha$-biphenylisopropyloxycarbonyl amino acid mixed anhydride.

6. A synthesis according to claim 1 wherein the insoluble support is a crosslinked polystyrene.

7. A synthesis according to claim 1 wherein the insoluble support is a crosslinked polyacrylamide.

8. A synthesis according to claim 1 wherein the synthesis is carried out in a flow reactor.

9. A synthesis according to claim 8 wherein the flow reactor is a pressurized, continuous flow reactor.

10. A synthesis according to claim 9 wherein the pressurized flow reactor is under a pressure of at least 40 psi.

* * * * *